United States Patent
Takeuchi et al.

(10) Patent No.: US 12,016,329 B2
(45) Date of Patent: Jun. 25, 2024

(54) FRAGILE OBJECT PRESERVING DEVICE PROVIDED WITH SEALING MECHANISM

(71) Applicant: TERUMO KABUSHIKI KAISHA, Tokyo (JP)

(72) Inventors: Ryohei Takeuchi, Kanagawa (JP); Toshikazu Takeuchi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 136 days.

(21) Appl. No.: 16/748,027

(22) Filed: Jan. 21, 2020

(65) Prior Publication Data
US 2020/0154698 A1 May 21, 2020

Related U.S. Application Data

(63) Continuation of application No. PCT/JP2018/027215, filed on Jul. 20, 2018.

(30) Foreign Application Priority Data

Jul. 20, 2017 (JP) .................................. 2017-141179

(51) Int. Cl.
*A01N 1/02* (2006.01)
*B65D 53/02* (2006.01)
(Continued)

(52) U.S. Cl.
CPC ........... *A01N 1/0242* (2013.01); *A01N 1/021* (2013.01); *B65D 53/02* (2013.01); *B65D 81/24* (2013.01); *C12M 23/38* (2013.01); *C12M 23/48* (2013.01)

(58) Field of Classification Search
CPC .... A01N 1/021; A01N 1/0242; A01N 1/0263; B65D 53/02; B65D 81/24; C12M 1/14; C12M 3/00; C12M 23/38; C12M 23/48
See application file for complete search history.

(56) References Cited

U.S. PATENT DOCUMENTS 4,988,302 A * 1/1991 Smith ..................... C12M 23/10
435/305.4
6,040,153 A * 3/2000 Lemonnier ............. C12M 41/36
435/305.4
(Continued)

FOREIGN PATENT DOCUMENTS

JP 2001224355 * 8/2001
JP 2004113776 A 4/2004
(Continued)

OTHER PUBLICATIONS

JP 2007119033 A Espacenet Translation (Provided by Espacenet on Jul. 8, 2021) (Year: 2007).*
(Continued)

*Primary Examiner* — Holly Kipouros
*Assistant Examiner* — Nathan G Esperon
(74) *Attorney, Agent, or Firm* — BUCHANAN INGERSOLL & ROONEY PC

(57) ABSTRACT

A technique is disclosed for preserving a shape of a fragile object in a liquid. The technique includes a device including a container that houses a fragile object and has a cylindrical shape including a bottom, a lid that seals the container, and a seal. The container includes a lower portion that houses the fragile object, an upper portion that includes an opening, and a stepped portion provided between the lower portion and the upper portion. The lid seals the opening of the upper portion. The seal is interposed between the lid and the stepped portion to seal an opening of the lower portion.

20 Claims, 2 Drawing Sheets

(51) Int. Cl.
  *B65D 81/24* (2006.01)
  *C12M 1/00* (2006.01)
  *C12M 3/00* (2006.01)

(56) References Cited

U.S. PATENT DOCUMENTS

| | | | | |
|---|---|---|---|---|
| 6,156,566 | A * | 12/2000 | Bryant | C12M 21/06 435/373 |
| 8,703,074 | B2 * | 4/2014 | Nozaki | A01N 1/0263 422/547 |
| 8,919,554 | B2 * | 12/2014 | Huldin | B65D 51/00 206/366 |
| 8,999,703 | B2 * | 4/2015 | Welch | C12M 23/08 435/283.1 |
| 11,420,805 | B2 * | 8/2022 | Takeuchi | A01N 1/0263 |
| 2007/0212750 | A1 * | 9/2007 | Kieffer | C12M 29/04 435/287.1 |
| 2009/0272748 | A1 * | 11/2009 | Welch | C12M 41/44 220/501 |
| 2015/0231628 | A1 * | 8/2015 | Nozaki | B01L 3/508 53/473 |

FOREIGN PATENT DOCUMENTS

| | | | | |
|---|---|---|---|---|
| JP | 2004317957 | * | 11/2004 | |
| JP | 2007-119033 | A | 5/2007 | |
| JP | 2007119033 | A * | 5/2007 | C12M 45/22 |
| JP | 2007269327 | A | 10/2007 | |
| JP | 2009089715 | A | 4/2009 | |
| JP | 2012041052 | A | 3/2012 | |
| JP | 2012130311 | A | 7/2012 | |
| WO | 2009/136907 | A1 | 11/2009 | |
| WO | WO-2009136907 | A1 * | 11/2009 | A01N 1/0273 |
| WO | 2014041593 | A1 | 3/2014 | |
| WO | WO-2017051650 | A1 * | 3/2017 | |

OTHER PUBLICATIONS

Oie et al., "Development of a Cell Sheet Transportation Technique for Regenerative Medicine," Tissue Engineering: Part C, (May 2014), vol. 20, No. 5, pp. 373-382.

The extended European Search report dated Jul. 6, 2020, by the European Patent Office in corresponding European Patent Application No. 18834679.5-1122. (10 pages).

International Search Report (with English Translation) and Written Opinion issued in corresponding International Patent Application No. PCT/JP2018/027215, 12 pages (dated Sep. 24, 2018).

* cited by examiner

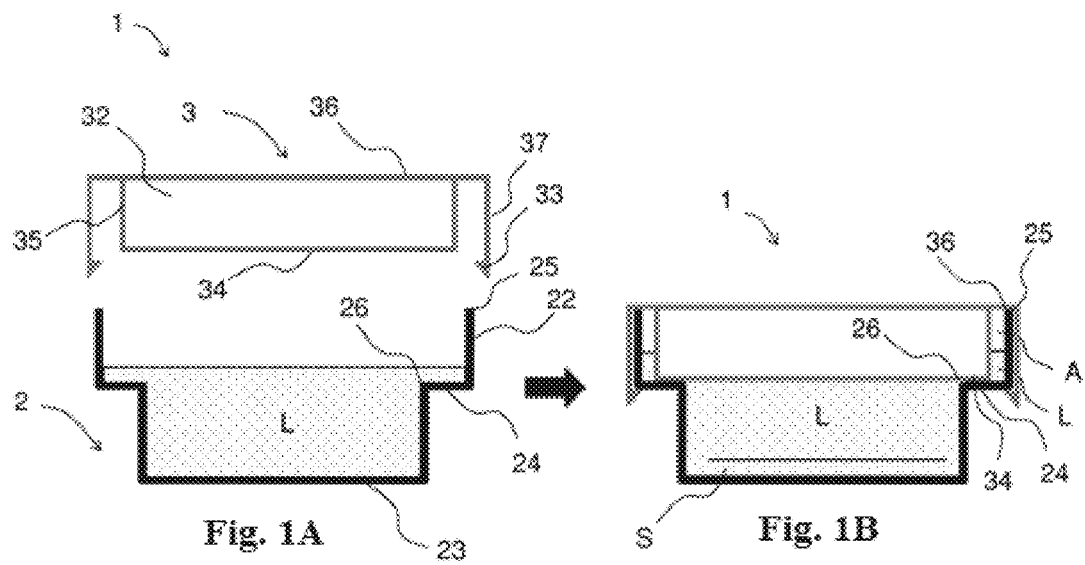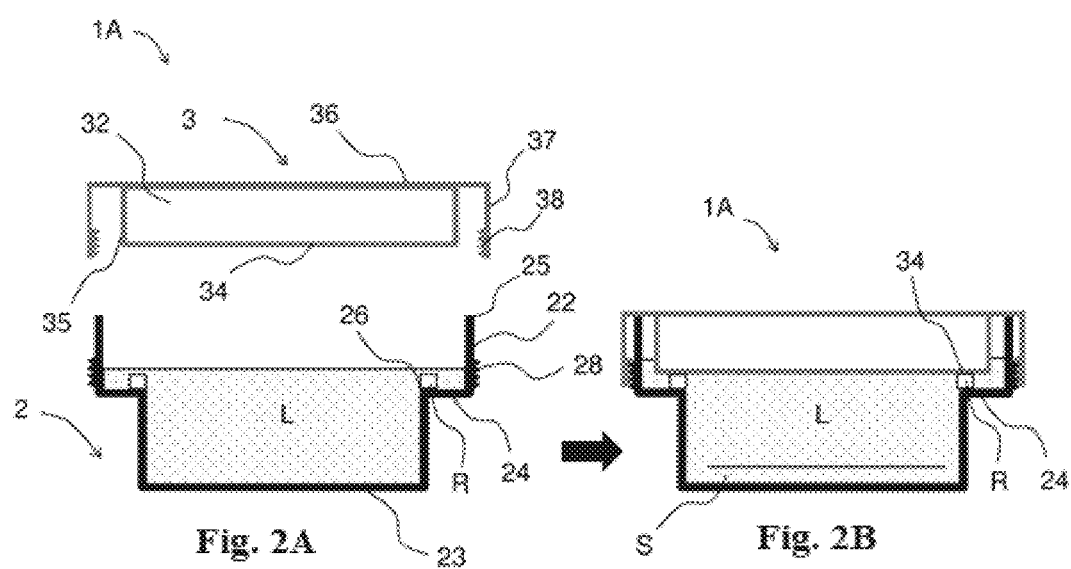

FRAGILE OBJECT PRESERVING DEVICE PROVIDED WITH SEALING MECHANISM

CROSS-REFERENCES TO RELATED APPLICATIONS

This application is a continuation of International Application No. PCT/JP2018/027215 filed on Jul. 20, 2018, which claims priority to Japanese Application No. 2017-141179 filed on Jul. 20, 2017, the entire content of both of which is incorporated herein by reference.

FIELD OF THE DISCLOSURE

The present disclosure generally relates to a fragile object preserving device provided with a sealing mechanism.

BACKGROUND DISCUSSION

In recent years, new regenerative healthcare is being developed as a solution for severe heart failure. For example, there is a new approach to severe cardiac infarction based on tissue engineering. In the new approach, a temperature-responsive culture dish is used to prepare a sheet cell culture, and the sheet cell culture is applied to a heart surface. The technique using a sheet cell culture helps enable a relatively safe transplant of a large amount of cells over a wide range and is particularly effective for treatment of cardiac diseases (such as heart failure, particularly, chronic heart failure) associated with, for example, cardiac infarction (including chronic heart failure associated with cardiac infarction), dilated cardiomyopathy, ischemic cardiomyopathy, and systolic dysfunction (such as left ventricular systolic dysfunction).

In order to apply such a sheet cell culture to clinical trials, it is required, for example, to store a prepared sheet cell culture together with a preservative solution inside a container and carry the cell culture to an intensive care unit or the like where transplantation is to be performed. However, a sheet cell culture is relatively low in absolute physical strength, and vibrations caused by carrying a container may wrinkle, break, or damage the sheet cell culture. For this reason, carrying a sheet cell culture requires highly-advanced techniques and extreme care.

In order to accommodate those needs, various methods and containers are being developed. For example, JP 2012-130311 A discloses a container for storing and transporting a membrane tissue. In the container, a storage is filled with a preservative solution to such an extent as to prevent formation of a gas layer. Accordingly, the preservative solution can be prevented from rippling or flowing, and consequently, the membrane tissue is not affected by vibrations and protected from damages.

JP 2007-269327 A discloses a packaging container for a cultured tissue. The packaging container includes a container body, a lid, and an inner tray on which a cultured tissue is to be placed. In the packaging container, a cultured tissue is placed and housed in the inner tray, and an inner tray operation unit is prepared in advance inside the packaging container. With such a structure, the packaging container facilitates ejection of the inner tray from the container body. However, the use of the packaging container may allow bubbles to remain inside the packaging container.

Furthermore, JP 2009-89715 A discloses a package for carrying a cultured cell sheet. When the package is sealed with a lid, air and a small amount of liquid medium are removed from the package. Accordingly, even though the package for a cultured cell sheet is shaken while being carried, bubbles do not move inside the liquid medium, and the cultured cell sheet can be prevented from being deviated or chipped.

SUMMARY

Under the circumstances, a technique for preserving a shape of a fragile object in a liquid has been developed. Accordingly, a device for preserving a shape of a fragile object in a liquid is disclosed.

In accordance with an aspect, it has been found that dimensional deviation of a container or a lid during a production process makes it relatively difficult to form a liquid-tight space successfully. As a result, it has been found that the problem can be solved by providing a seal between a container and a lid.

[1] In accordance with an aspect, a device is disclosed including: a container that houses a fragile object, the container having a cylindrical shape including a bottom; a lid that seals the container; and a seal, wherein the container includes a lower portion that houses the fragile object; an upper portion that includes an opening; and a stepped portion provided between the lower portion and the upper portion, the lid seals the opening of the upper portion, and the seal is interposed between the lid and the stepped portion to seal an opening of the lower portion.

[2] The device according to [1], wherein the upper portion has an inside diameter larger than an inside diameter of the lower portion, and the stepped portion is a portion where an inside diameter of the container is sharply reduced.

[3] The device according to [1] or [2], wherein the seal includes a packing ring between the seal and the stepped portion.

[4] The device according to any one of [1] to [3], wherein the packing ring has a groove perpendicular to the packing ring in a circumferential direction.

[5] The device according to any one of [1] to [4], wherein the seal is pressed by the lid and the stepped portion when the lid is screwed onto the container.

[6] The device according to any one of [1] to [5], wherein the opening of the upper portion is sealed with the lid simultaneously with or after sealing of the opening of the lower portion by the seal.

[7] The device according to any one of [1] to [6], wherein the fragile object is a sheet cell culture.

[8] The device according to any one of [7], wherein the sheet cell culture is a laminated body.

In accordance with another aspect, a device according to the present disclosure reliably creates a liquid-tight space inside a container and does not allow bubbles (gas) to enter the container. Accordingly, even when the container is shaken, a fragile object is not damaged by motion of bubbles inside the container. For example, when the fragile object is a laminated body of sheet cell cultures, the laminated body is not deviated or chipped by motion of bubbles. In addition, even though dimensions of a container or a lid are deviated during a production process, the container can be reliably closed in a liquid-tight manner, which gives a great advantage in terms of design cost and production cost.

In accordance with another aspect, a device is disclosed, the device comprising: a container configured to house a fragile object, the container having a cylindrical shape including a bottom, the container including a lower portion configured to house the fragile object, an upper portion that includes an opening, and a stepped portion provided between the lower portion and the upper portion; a lid configured to seal the opening of the upper portion of the container; and a seal, the seal being interposed between the lid and the stepped portion to seal an opening of the lower portion.

In accordance with an aspect, a device is disclosed, the device comprising: a container, the container having a cylindrical shape including a round bottom, a lower portion, an upper portion having an opening, and an annular stepped portion extending from the lower portion of the container to the upper portion of the container; a lid configured to seal the opening of the upper portion of the container; and a seal, the seal being interposed between the lid and the stepped portion to seal an opening of the lower portion.

In accordance with another aspect, a method is disclosed for preserving a fragile object, the method comprising: pouring a liquid in a lower portion of a container until the liquid rises above a stepped portion, the stepped portion being between a lower portion of the container and an upper portion of the container; placing the fragile object into the liquid in the container; interposing a seal between a lid configured to seal an opening of the upper portion of the container and the stepped portion; and covering the container with the lid and the seal to raise a level of the liquid in the lower portion of the container and pushing the liquid from the container into a space between an outer periphery of the seal and an inner periphery of the container until a bottom surface of the seal and the stepped portion come into contact with each other.

BRIEF DESCRIPTION OF THE DRAWINGS

FIGS. 1A and 1B are cross-sectional views of a device according to a first embodiment of the present disclosure.

FIGS. 2A and 2B are cross-sectional views of a device according to a first modification of the first embodiment.

DETAILED DESCRIPTION

Figures 3A, 3B:
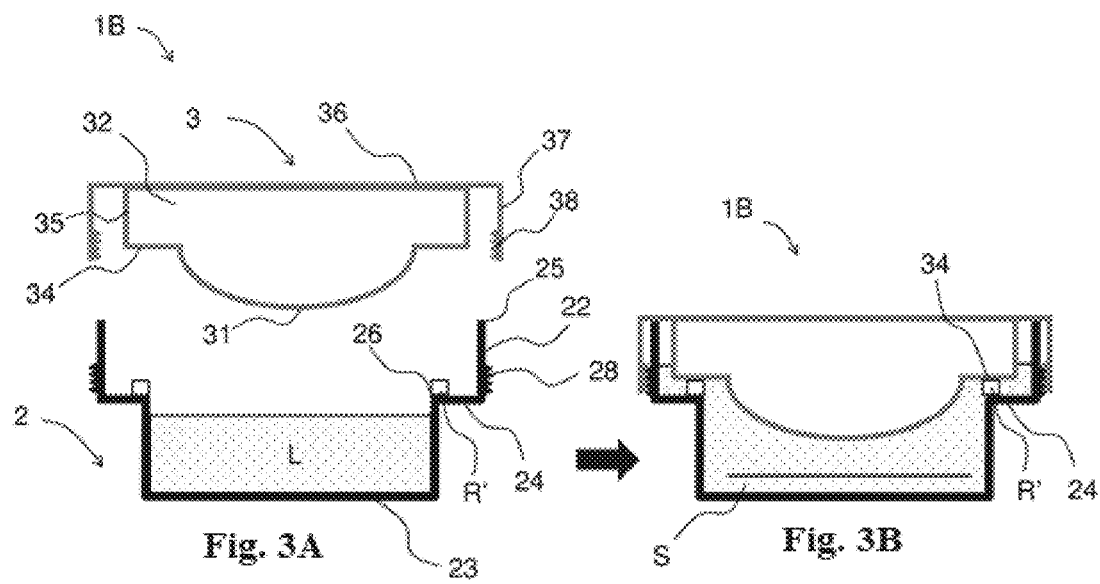
FIGS. 3A and 3B are cross-sectional views of a device according to a second modification of the first embodiment.

Set forth below with reference to the accompanying drawings is a detailed description of embodiments of a fragile object preserving device provided with a sealing mechanism representing examples of the inventive fragile object preserving device provided with a sealing mechanism.

An aspect of the present disclosure relates to a device including: a container that houses a fragile object, the container having a cylindrical shape including a bottom; a lid that seals the container; and a seal, wherein the container includes a lower portion that houses the fragile object; an upper portion that includes an opening; and a stepped portion provided between the lower portion and the upper portion, the lid seals the opening of the upper portion, and the seal is interposed between the lid and the stepped portion to seal an opening of the lower portion.

The fragile object herein represents an object that has relatively low physical strength and may be broken, damaged, or deformed by, for example, liquid vibration. Such an object may be, for example, one provided with a relatively thin portion, one having a band shape, or one having a sheet shape. The object having a sheet shape is not particularly limited and may be a sheet structure. Examples of the sheet structure include flat membrane tissues made of biological materials such as sheet cell cultures and various kinds of films made of plastic, paper, woven fabric, non-woven fabric, metals, polymers, or lipids. Among these examples of the sheet structure, objects that are persistent or hardly dissolved in a liquid are preferable. The sheet structure may be polygonal or circular and does not necessarily have a uniform width, thickness, diameter, and the like. The sheet structure used in the present disclosure may be a single layer including one sheet or a laminated body including two or more sheets. In the latter case, layers of the laminated body may be, but are not necessarily, connected to each other. In a case where the layers are connected, overlapping parts may be connected thoroughly or partially. The term "fragile" according to the present disclosure indicates that an object is so vulnerable that it is difficult or substantially impossible to evaluate tensile properties of the object, for example, by a tension testing machine in the related art (for example, one described in JIS K 7161 (i.e., Japanese Standards Association (JSA), Plastics—Determination of Tensile Properties) in which the object is fixed to a gripping tool outside a liquid. Examples of the fragile object include those having a small value of each tensile property or those having difficulty in measuring tensile properties correctly with a tensile testing machine in the related art. Examples of the fragile object include those showing, in a tensile test, a breaking load of less than 10 N (Newton), less than 5 N, less than 2 N, less than 1 N, less than 0.5 N, less than 0.1 N, and less than 0.05 N. The limit of a breaking load measured by a tensile test in the related art is generally about 1 N. For this reason, in an aspect of the present disclosure, it is preferable to use an object that shows a breaking load lower than 1 N (for example, less than 0.5 N) as the fragile object.

The fragile object herein includes, for example, a biological transplant having relatively low physical strength, and examples of the biological transplant include cultured cells (for example, cell cultures) or collected cells. Another examples of the transplant include products produced by cells. In addition to cells and/or products of cells, examples of the biological transplant can include materials (prosthesis and supporting materials) for replacing and/or supporting a predetermined part (for example, an affected part) of a living body. The biological transplant may have various kinds of shapes such as a sheet shape, a film shape, a lump shape, and a column shape. The biological transplant is used for transplantation into a living body. A specific example of the biological transplant is a sheet cell culture.

In accordance with an aspect, the sheet cell culture herein represents cells connected to each other to form a sheet shape. Cells may be connected to each other directly (including cells with cellular elements such as adhesion molecules involved) and/or with an intervening substance involved. The intervening substance is not particularly limited as long as the substance connects cells at least physically (mechanically). An example of the intervening substance includes an extracellular matrix. The intervening substance is preferably derived from cells, particularly, cells that form a sheet cell culture. The cells are at least physically (mechanically) connected to each other but may be connected functionally, for example, chemically or electrically. The sheet cell culture may include one cell layer (monolayer) or may include two or more cell layers (multilayer body). Furthermore, the sheet cell culture does not necessarily have a clear layer structure (i.e., uniformly arranged in a vertical direction), and may, for example, have a three-dimensional structure with a thickness exceeding a thickness of one cell. For example, in the perpendicular cross section of the sheet cell culture, cells may be arranged non-uniformly (for example, in a mosaic manner) without being aligned uniformly in the horizontal direction. The sheet cell culture may exist as a single (one) sheet cell culture formed independently or exist as a laminated body having two or more independent single (one) sheet cell cultures being laminated. The laminated body may have sheet cell cultures laminated in, for example, two layers (two sheets), three layers (three sheets), four layers (four sheets), five layers (five sheets), or six layers (six sheets).

The sheet cell culture herein includes any kind of cells that may form the aforementioned structure. Examples of the cells include, but are not limited to, adherent cells (adhesive cells). Examples of the adherent cells include adherent somatic cells (such as cardiac muscle cells, fibroblast cells, epithelial cells, endothelial cells, hepatic cells, pancreatic cells, renal cells, adrenal cells, periodontal ligament cells, gingival cells, periosteal cells, skin cells, synovial cells, and cartilage cells) and stem cells (for example, tissue stem cells such as myoblast cells and cardiac stem cells; embryonic stem cells; pluripotent stem cells such as induced pluripotent stem (iPS) cells; and mesenchymal stem cells). Somatic cells may be differentiated from stem cells, particularly, from iPS cells. Examples of cells that form a sheet cell culture include, but are not limited to, myoblast cells (such as skeletal myoblast cells), mesenchymal stem cells (such as bone marrow, adipose tissue, peripheral blood, skin, hair roots, muscular tissue, endometrium, placenta, and cells derived from cord blood), cardiac muscle cells, fibroblast cells, cardiac stem cells, embryonic stem cells, iPS cells, synovial cells, cartilage cells, epithelial cells (such as oral mucosal epithelial cells, retinal pigment epithelial cells, and nasal mucosal epithelial cells), endothelial cells (such as vascular endothelial cells), hepatic cells (such as hepatic parenchymal cells), pancreatic cells (such as islet cells), renal cells, adrenal cells, periodontal ligament cells, gingival cells, periosteal cells, and skin cells. Herein, preferable examples are cells that form a monolayer cell culture, such as myoblast cells or cardiac muscle cells, and skeletal myoblast cells or iPS cell-derived cardiac muscle cells are particularly preferable.

The cells may be derived from any organism treatable with a cell culture. Examples of the organism include, but are not limited to, humans, non-human primates, dogs, cats, pigs, horses, goats, and sheep. Furthermore, one type of cell or two or more types of cells may be used for forming a sheet cell culture. In a preferred aspect of the present disclosure, when the number of cells that form a cell culture is two or more, a ratio (purity) of the greatest number of cells, for example, a ratio of skeletal myoblast cells, is 65% or more, preferably 70% or more, and more preferably 75% or more, at the end of producing the cell culture.

The sheet cell culture according to the present disclosure may be a sheet cultured tissue obtained by inoculating and culturing cells in a scaffold (scaffold during cell culturing). However, the sheet cell culture is preferably composed of a material derived from a cell that forms a cell culture and does not include other materials.

The sheet cell culture may be produced by any known technique.

In an aspect of the present disclosure, the sheet cell culture is a sheet skeletal myoblast cell culture. The reason is that maintaining a shape of a sheet skeletal myoblast cell culture in a liquid is of great significance since a sheet skeletal myoblast cell culture is so fragile that it breaks by its own weight when a part of the cell culture is grabbed and that such fragility not only disables the cell culture to be carried independently but also makes it extremely difficult for the cell culture to return to the original shape when it is once folded.

The container herein is not specifically limited as long as the container houses a fragile object, a liquid, and the like and helps prevent the liquid from leaking. The container herein may be of any type, and a commercially available container may also be used. Examples of a material of the container include, but are not limited to, polyethylene, polypropylene, Teflon (registered trademark), polyethylene terephthalate, polymethyl methacrylate, nylon 6,6, polyvinyl alcohol, cellulose, silicone, polystyrene, glass, polyacrylamide, polydimethylacrylamide, and metals (such as iron, stainless steel, aluminum, copper, and brass). In addition, the container preferably has at least one flat bottom surface for maintaining a shape of the fragile object. Examples of the container include, but are not limited to, a petri dish, a cell culture dish, and a cell culture bottle. The flat bottom surface has an area of, for example, $1.13$ $cm^2$ to $78.5$ $cm^2$, preferably $12.6$ $cm^2$ to $78.5$ $cm^2$, and more preferably $9.1$ $cm^2$ to $60.8$ $cm^2$ but is not limited to the area as disclosed.

Herein, the liquid inside the container includes at least one component. The component is not particularly limited, and examples of the component include water, aqueous solution, non-aqueous solution, suspension, and emulsion.

The solution or liquid herein may be a fluid having fluidity as a whole and may include solid substances such as cell scaffolds and other non-liquid components such as bubbles.

The component included in the liquid inside the container is not particularly limited as long as the component has little influence on the fragile object. In a case where the fragile object is a membrane including a biological material-derived material, the component included in the liquid inside the container is preferably biocompatible from a viewpoint of biological stability and long-term storage. In accordance with an aspect, the component included in the liquid is preferably one that does not cause undesired effects such as inflammatory reactions, immune reactions, and intoxicating reactions against living tissue or cells, or one that causes such effects to a small extent. Examples of the component include water, saline, physiological buffers (such as HBSS, PBS, EBSS, Hepes, and sodium bicarbonate), media (such as DMEM, MEM, F12, DMEM/F12, DME, RPMI1640, MCDB, L15, SkBM, RITC80-7, and IMDM), carbohydrate solutions (such as sucrose solution and Ficoll-paque PLUS (registered trademark)), seawater, serum-containing solution, Renografin (registered trademark) solution, metrizamide solution, meglumine solution, glycerin, ethylene glycol, ammonia, benzene, toluene, acetone, ethyl alcohol, benzol, oil, mineral oil, animal fat, vegetable oil, olive oil, colloidal solution, liquid paraffin, turpentine oil, linseed oil, and castor oil.

In a case where the fragile object is a sheet cell culture, the component included in the liquid inside the container is preferably one that helps enable stable storage of cells, contains the minimal amount of oxygen and nutrients necessary for cell survival, and does not break cells due to osmotic pressure or the like. Examples of the component include, but are not limited to, physiological saline, physiological buffers (such as HBSS, PBS, EBSS, Hepes, and sodium bicarbonate), media (such as DMEM, MEM, F12, DMEM/F12, DME, RPMI1640, MCDB, L15, SkBM, RITC80-7, and IMDM), and carbohydrate solutions (such as sucrose solution and Ficoll-paque PLUS (registered trademark)).

The lid as disclosed herein is not particularly limited as long as the lid seals the container. Examples of a material of the lid include, but are not limited to, polyethylene, polypropylene, Teflon (registered trademark), polyethylene terephthalate, polymethyl methacrylate, nylon 6,6, polyvinyl alcohol, cellulose, silicone, polystyrene, glass, polyacrylamide, polydimethylacrylamide, and metals (such as iron, stainless steel, aluminum, copper, and brass).

In accordance with an aspect, the container has a cylindrical shape including a bottom. In accordance with an aspect, the horizontal section of the cylindrical container is not particularly limited in shape as long as the container has at least one flat bottom surface for maintaining a shape of the fragile object. For example, the container may be shaped into a triangle, a rectangle, a polygon, a circle, and an ellipse. The lid is not particularly limited in shape as long as the lid and the container are engaged to create a sealed space. For example, in a case where the container is a general-purpose petri dish, the lid preferably has a circular shape. Furthermore, the lid and/or the container may include a light transmissive material to make it possible to check the state of the fragile object housed in the container and the presence or absence of bubbles in the liquid.

Herein, the lower portion of the container represents the lower side of the container having the flat bottom surface that houses a liquid, a gas, a fragile object, or the like, and the upper portion of the container represents the upper side of the container, that is, a space between the opening and the lower portion of the container. The stepped portion of the container represents a boundary between the lower portion and the upper portion, that is, a part where an inside diameter of the container sharply decreases or a tapered part where the inside diameter increases from the lower portion toward the upper portion. In accordance with an aspect, the stepped portion has an annular surface with a width obtained by a difference between the inside diameter of the lower portion and the inside diameter of the upper portion. The space in the lower portion represents a housing space surrounded by the lower portion of the container, and the space in the upper portion represents a space surrounded by the upper portion of the container. The opening 26 of the space in the lower portion represents a boundary edge between the space in the lower portion and the stepped portion, and the opening 25 of the space in the upper portion represents an edge of the container, that is, an end of the space in the upper portion.

The seal herein represents a portion that is interposed between the lid and the stepped portion and seals the opening 26 in the lower portion when the lid is attached to the container. The seal has an outside diameter smaller than the inside diameter of the upper portion of the container so as to be inserted into the opening 25 of the upper portion of the container. Furthermore, the outside diameter of the seal is larger than the inside diameter of the lower portion of the container so as not to be inserted into the opening 26 of the lower portion of the container. Therefore, the bottom surface of the seal comes into contact with the stepped portion so as to create a sealed space surrounded by the bottom surface of the seal and the inner surface of the lower portion. In addition, there is a space between an outer periphery of the seal and an inner periphery of the upper portion of the container. Accordingly, using this space as a channel, the liquid and gas in the lower portion of the container can be discharged from the opening 25 in the upper portion of the container. In this manner, it is not required to accurately design the container and the lid to make the seal of the lid come into contact with the inner periphery of the container. Accordingly, even though dimensions of the container or the lid are deviated during a production process, the container can be reliably closed in a liquid-tight manner.

In accordance with an aspect, the seal herein may be a part of the lid or may be a separate member from the lid. For example, when a sealing member such as a packing ring is interposed, as a separate member, between the seal and a container, the seal includes a packing ring. A material of the seal may be a rigid body or an elastic body as long as the material enables sealing of the edge of the container, but an elastic body is preferable. The elastic body is not particularly limited and may be, for example, silicone, plastic, or rubber. The packing ring is not particularly limited in cross section and may be shaped into, for example, a triangle, a quadrangle, a polygon, a circle, or an ellipse. The packing ring preferably has a triangular cross section, since it is easier to deform the packing ring when a pressing force is applied to a vertex.

The protrusion herein represents, for example, a member having a protruding portion or a member having a bulging portion, that is, a member including a non-flat portion. The protrusion protruding toward the space in the lower portion indicates that the protrusion protrudes to such an extent as to push out the liquid and gas in the lower space of the container. Those skilled in the art may freely set the size of the protrusion according to the amount or volume of the liquid.

Herein, a horizontal sectional area of the protrusion represents, for example, an area of the two-dimensional cross section which appears when the protrusion is cut at the liquid level while protrusion is immersed in the liquid. Accordingly, the expression "the horizontal sectional area of the protrusion tapers perpendicularly downward" indicates that, when the protrusion is immersed in the liquid while being descended perpendicularly downward from the top of the liquid, a contact area between the protrusion and the liquid gradually increases.

In an aspect of the present disclosure, the protrusion has a dome shape and including a vertex, and preferably, the protrusion is designed to have a vertex intersecting the center line of the lid and the center line of the container. The curved protrusion may have a hyperboloid shape, a paraboloid shape, a hemispherical shape, a conical surface shape, or a pyramidal shape, but is not limited to a hyperboloid shape, a paraboloid shape, a hemispherical shape, a conical surface shape, or a pyramidal shape.

Hereinafter, preferred embodiments of the present disclosure will be described in detail with reference to the drawings.

First Embodiment

First, a first embodiment of the present disclosure will be described.

Figures 4A, 4B:
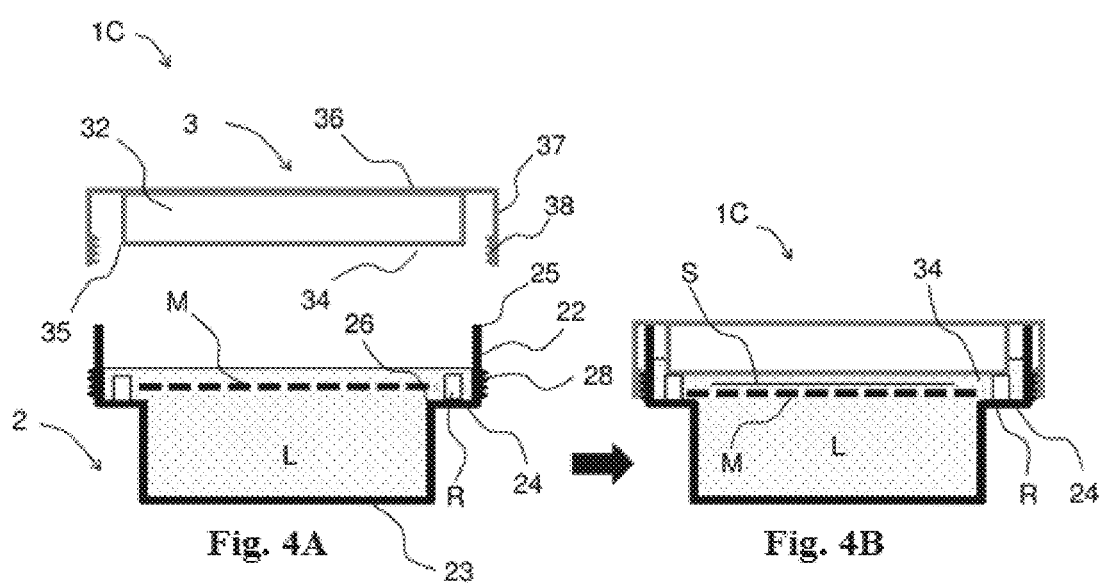
FIGS. 4A and 4B are cross-sectional views of a device according to a third modification of the first embodiment.

FIGS. 1A and 1B are cross-sectional views of a device according to the first embodiment of the present invention. FIGS. 2A and 2B are cross-sectional views of a device according to a first modification of the first embodiment. FIGS. 3A and 3B are cross-sectional views of a device according to a second modification of the first embodiment. FIGS. 4A and 4B are cross-sectional views of a device according to a third modification of the first embodiment. In each drawing in this application, for the purpose of illustration, note that sizes of the illustrated members are emphasized as appropriate and are different from the actual sizes.

As shown in FIG. 1A, a device 1 according to the first embodiment of the present disclosure includes a container 2 and a lid 3 that seals the container 2. The container 2 is a round container that has a cylindrical shape including a bottom. The container 2 includes an upper portion 22 and a lower portion 23. The lower portion 23 includes a housing space that houses a fragile object S and the like. The upper portion 22 has an inside diameter (i.e., inner diameter) larger than an inside diameter (i.e., inner diameter) of the lower portion 23. A stepped portion 24, or a part where the inside diameter (i.e., inner diameter) of the container sharply decreases, is disposed at a boundary between the upper portion 22 and the lower portion 23. The stepped portion 24 has an annular shape parallel to a bottom surface of the container 2. The lid 3 includes a top board (or top) 36 that covers an opening 25 of the container 2. The container 2 is sealed when the lid 3 is attached to the container 2.

The lid 3 includes a seal 32 extending downward from the center of the top board 36 of the lid 3, a cylindrical sidewall (i.e., cylindrical skirt) 37 extending downward (i.e., drooping) from a peripheral edge of the top board 36, and an engagement portion 33 protruding and disposed on an inner surface of the cylindrical skirt 37. The seal 32 has a columnar shape, including a bottom surface 34 and an outer periphery 35. The seal 32 has an outside diameter (i.e., outer diameter) larger than the inside diameter of the lower portion 23 and smaller than the inside diameter of the upper portion 22. Therefore, when the seal 32 is inserted into the container 2, the bottom surface 34 of the seal 32 comes into contact with a surface of the stepped portion 24, which creates a space between the seal 32 and the upper portion 22. Furthermore, a height of the seal 32 from the top board 36 is substantially equal to a height of the upper portion 22. In other words, the device 1 includes a seal mechanism that enables sealing between the seal 32 and the stepped portion 24 and sealing between the top board 36 and the opening 25 almost at the same time when the lid 3 is attached to the container 2.

As shown in FIG. 1A, when the device 1 is used, a liquid L is poured into the container 2 until the liquid rises above the stepped portion 24, and then, the fragile object S is housed in the lower portion 23 of the container 2. As shown in FIG. 1B, when the container 2 is covered with the lid 3, the seal 32 travels inside the container 2. After the seal 32 reaches the liquid level, the seal 32 travels further downward. Then, the liquid L is pushed out into a space between the outer periphery 35 of the seal 32 and an inner periphery of the container 2, which raises the liquid level. When the liquid level rises, air A in the container 2 is pushed and discharged out of the container 2 from the opening 25. At this time, the top board 36 and the opening 25 are not in contact with each other, which enables the liquid L and the air A to move.

When the seal 32 travels further downward, the bottom surface 34 of the seal 32 and the stepped portion 24 come into contact with each other, which offers a liquid-tight space inside the housing space (the space in the lower portion 23). Almost at the same time, the top board 36 and the opening 25 come into contact with each other, which offers a sealed space inside the container 2 (the space in the upper portion 22). At this time, the liquid L and the gas (air) A exist in the space in the upper portion 22 of the container 2, but the container 2 is sealed triply (i.e., three contacts) by the top board 36 in contact with the opening 25, the cylindrical sidewall 37 in contact with the outer periphery of the container 2, and the engagement portion 33 that engages with a lower edge of the upper portion 22 of the container 2. Accordingly, the liquid L in the upper portion 22 does not flow out and maintains hygiene (i.e., maintains the liquid and object in a healthy and clean state). Therefore, it is preferable to prevent the liquid from leaking out of the container 2 by adjusting the liquid volume and capacity in advance so that the volume of the liquid pushed out of the container 2 is not larger than the capacity of the liquid-receiving space provided between the upper portion 22 of the container 2 and the lid 3.

In such a configuration, if the height of the seal 32 from the top board 36 is smaller than the height of the upper portion 22, the top board 36 and the opening 25 come into contact with each other before the seal 32 and the stepped portion 24 come into contact with each other. In this case, the space in the upper portion 22 is sealed first, leaving no space for the liquid L and the air A to move, which does not allow the seal 32 to travel any more. Accordingly, the space in the lower portion cannot be made liquid-tight. On the other hand, the device 1 according to this embodiment seals the space in the upper portion 22 with the lid 3 without preventing the seal 32 from sealing the space in the lower portion 23.

As described above, the device 1 according to the first embodiment of the present disclosure reliably creates a liquid-tight space inside a container and does not allow, for example, bubbles (gas) to enter the container. Accordingly, even when the container is shaken, a fragile object is not damaged by motion of bubbles inside the container. Particularly, when the fragile object is a laminated body of sheet cell cultures, the laminated body is not deviated or chipped by motion of bubbles.

This embodiment is not limited to the above device, and those skilled in the art may design devices having different configurations and shapes. For example, at least a part of the seal 32 of the lid 3 may include an elastic body, and a height of the seal 32 from the top board 36 may be made larger than a height of the upper portion 22. Furthermore, at least a part of the seal 32 may be a seal mechanism that presses and crushes the seal 32 between the lid 3 and the stepped portion 24 to reduce a height of the lid 3 after sealing the space in the lower portion 23 with the seal 32 and then seals the lid 3 and the opening 25 of the upper portion 22.

In this manner, with the device 1 according to the first embodiment of the present disclosure, even though dimensions of a container or a lid are deviated during a production process, the container can be reliably closed in a liquid-tight manner, which gives a great advantage in terms of design cost and production cost.

A first modification of the device 1 according to the first embodiment of the present disclosure will now be described. Hereinafter, differences from the first embodiment will be described in detail but similarities will not be described.

As shown in FIG. 2A, a device 1A according to the first modification includes a container 2 and a lid 3 that seals the container 2. An internal thread 38 is disposed on an inner periphery of a cylindrical sidewall 37. The internal thread 38 is screwed into an external thread 28 disposed on an outer periphery of an upper portion 22 of the container 2. When the container 2 is covered with the lid 3, and the internal thread 38 is screwed into the external thread 28, the lid 3 is connected to the container 2 with pressure (i.e., physical force). In this modification, a height of a seal 32 from a top board 36 is slightly smaller than a height of the upper portion 22. Furthermore, an elastic packing ring R is disposed between the seal 32 and a stepped portion 24.

As shown in FIG. 2A, when the device 1A is used, a liquid L is poured into the container 2 until the liquid rises above the packing ring R, and then, a fragile object S is housed inside a lower portion 23 of the container 2. As shown in FIG. 2B, when the lid 3 is attached to the container 2, and the internal thread 38 is screwed into the external thread 28, the seal 32 travels inside the container 2, and the seal 32 is brought into contact with the packing ring R. Accordingly, a liquid-tight space is created inside the lower portion 23. When the lid 3 is screwed onto the container 2, the packing ring R is pressed and crushed by the seal 32, and the top board 36 is brought into contact with an opening 25. Accordingly, the container 2 is sealed.

As described above, the first modification of the device 1 according to the first embodiment of the present disclosure reliably creates a liquid-tight space inside a container and does not allow bubbles (gas) to enter the container. Accordingly, even when the container is shaken, a fragile object is not damaged by motion of bubbles inside the container. Particularly, when the fragile object is a laminated body of sheet cell cultures, the laminated body is not deviated or chipped by motion of bubbles. In addition, even though dimensions of a container or a lid are deviated during a production process, the container can be reliably closed in a liquid-tight manner, which gives a great advantage in terms of design cost and production cost.

Next, a second modification of the device 1 according to the first embodiment of the present disclosure will be described. Hereinafter, differences from the first modification of the first embodiment will be described in detail but similarities will not be described.

As shown in FIG. 3A, a device 1B according to a second modification includes a container 2 and a lid 3 that seals the container 2. In this modification, the lid 3 includes a protrusion 31 that protrudes downward from a bottom surface 34 of a seal 32 when the lid 3 is attached to the container 2. The protrusion 31 has a dome shape, including a vertex that has a horizontal sectional area tapering perpendicularly downward. The protrusion 31 pushes out a gas and a liquid inside a space in a lower portion 23 when the lid 3 is attached to the container 2. Furthermore, an upper end of the protrusion 31 has an outside diameter (i.e., outer diameter) smaller than an inside diameter of the lower portion 23 of the container 2 so as not to bring an outer periphery of the protrusion 31 into contact with an inner periphery of the container 2. On an upper surface of a packing ring R', a groove (not shown) is disposed in a direction perpendicular to the circumferential direction of the packing ring R'.

As shown in FIG. 3A, in this modification, when the device 1B is used, the amount of liquid L is not required to rise above a stepped portion 24. As shown in FIG. 3B, when the protrusion 31 disposed in the seal 32 travels inside the space in the lower portion, the gas and liquid inside the space in the lower portion 23 are pushed out by the protrusion 31 toward a space in an upper portion. At this time, a surface of the protrusion 31 is inclined relative to the liquid level (horizontal plane). Accordingly, buoyancy tends to be applied to bubbles and the like in the liquid, and the bubbles are pushed out. In addition, since the horizontal sectional area of the protrusion 31 tapers perpendicularly downward, a distance between the outer periphery of the protrusion 31 and the inner periphery of the lower portion 23 gradually reduces when the lid 3 is attached to the container 2. Accordingly, it is possible to push out the liquid L gently into the space in the upper portion 22 and to prevent the liquid L in the container 2 from flowing.

When the dome-shaped protrusion 31 is immersed in the liquid L, first, the vertex with a small area touches the liquid level, and then, the contact area gradually increases, which minimizes ripples of the liquid L in the container 2. The circular dome-shaped protrusion 31 pushes out the liquid L relatively uniformly and radially along the circular dome. Accordingly, the liquid L in the container 2 does not move in one direction in a radial direction, and consequently, the liquid L in the container 2 is prevented from flowing.

When the seal 32 travels further, the bottom surface 34 and the packing ring R' come into contact with each other, but the gas and liquid in the lower portion 23 move through the groove of the packing ring R'. Furthermore, when the lid 3 is screwed, the bottom surface 34 presses the packing ring R' and crushes the groove, whereby creating a liquid-tight space inside the container. In other words, in this modification, due to the groove disposed in the packing ring R', it is possible to crush the packing ring R' rather easily even when, for example, the space in the lower portion 23 is filled with a liquid. Here, if the packing ring R includes no groove, the liquid L has no space to move when a space F (not shown) surrounded by the bottom surface 34 of the seal 32, the packing ring R', and the lower portion 23 becomes liquid-tight. Accordingly, the liquid volume in the space F filled with the liquid L cannot be changed, that is to say, a height of the packing ring R' cannot be reduced. Therefore, it becomes rather difficult to seal an opening 25 of the container 2.

As described above, the second modification of the device 1 according to the first embodiment of the present disclosure reliably creates a liquid-tight space inside a container and does not allow bubbles (gas) to enter the container. Accordingly, even when the container is shaken, a fragile object is not damaged by motion of bubbles inside the container. Particularly, when the fragile object is a laminated body of sheet cell cultures, the laminated body is not deviated or chipped by motion of bubbles. In addition, even though dimensions of a container or a lid are deviated during a production process, the container is reliably closed in a liquid-tight manner, which gives a great advantage in terms of design cost and production cost.

Next, a third modification of the device 1 according to the first embodiment of the present disclosure will be described. Hereinafter, differences from the first embodiment will be described in detail but similarities will not be described.

As shown in FIG. 4A, a device 1C according to the third modification includes a container 2, a lid 3 that seals the container 2, a packing ring R, and a mesh plate M. In this modification, the packing ring R has a diameter smaller than an inside diameter of an upper portion 22 of the container 2 and larger than an inside diameter of a lower portion 23. The mesh plate M has a mesh network and allows a liquid L to pass through the mesh network of the mesh plate M. The mesh plate M has a diameter larger than the inside diameter of the lower portion 23 of the container 2 and smaller than the diameter of the packing ring R so that the mesh plate M is placed on a stepped portion 24.

As shown in FIG. 4B, when using the device 1C, the mesh plate M is placed on the stepped portion 24 of the container 2, and then, a fragile object S and the liquid L are put in the container 2. At this time, the liquid L passes through the mesh plate M, but the fragile object S remains on the mesh plate M. Furthermore, the liquid L is poured into the container 2 until the liquid rises above the packing ring R. Then, the container 2 is sealed with the lid 3 to create a liquid-tight space. As shown in the drawing, the fragile object S is preserved in the liquid-tight space between the mesh plate M and the seal 32 of the lid 3. When using the fragile object S, the lid 3 is removed, and the mesh plate M is taken out. Accordingly, the fragile object S can be taken out of the container 2 without being directly grabbed, which minimizes damage of the fragile object S.

Although the present disclosure has been described with reference to the illustrated embodiments, the present disclosure is not limited to the illustrated embodiments. For example, an annular dent (i.e., annular groove or annular recess) for receiving the packing ring R or R' may be disposed on a lower surface of the seal 32, and the packing ring R or R' may be allowed to fit into the dent (i.e., groove or recess). Such a structure makes the lower surface of the seal 32 level with a lower surface of the packing ring R or R' and makes it difficult for bubbles to remain inside the container.

Furthermore, for example, a recess may be disposed in the stepped portion of the container, and the recess may hold a liquid pushed out from the container. With such a structure, even when the lid is removed, the liquid held in the recess does not return to the container. Accordingly, it is possible to prevent not only a flow of the liquid in the container but also contamination of a fragile object. Still further, a packing ring may be interposed between the lid and the edge of the container so as to enhance sealing performance.

In the present disclosure, each component may be replaced with any component that exhibits similar function. Alternatively, any component may be added to any component.

The detailed description above describes embodiments of a fragile object preserving device provided with a sealing mechanism. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A device, the device comprising:
a container configured to house a fragile object, the container having a cylindrical shape including a bottom, the container including a lower portion configured to house the fragile object in a liquid that rises above a stepped portion of the container, an upper portion that includes an opening, and the stepped portion provided between the lower portion and the upper portion, the stepped portion including an annular surface having a width obtained by a difference between an inside diameter of the upper portion of the container and an inside diameter of the lower portion of the container;
a packing ring configured to be received on the annular surface of the stepped portion of the container, the packing ring having a diameter smaller than the inside diameter of the upper portion of the container and larger than the inside diameter of the lower portion of the container;
a lid configured to seal the opening of the upper portion of the container;
a seal, the seal representing a portion being interposed between the lid and the stepped portion, the seal extending from the lid and having an outside diameter larger than the inside diameter of the lower portion of the container, and wherein the outside diameter of the seal is smaller than an inside diameter of the upper portion of the container, such that, upon inserting the seal into the container, a space is created between an outer periphery of the seal, an outer periphery of the packing ring, and an inner periphery of the upper portion of the container, and wherein the seal is configured to seal an opening of the lower portion of the container by a bottom surface of the seal coming into contact with the packing ring on the annular surface of the stepped portion;
wherein the inside diameter of the upper portion of the container is larger than the inside diameter of the lower portion of the container, and the stepped portion is a portion where an inside diameter of the container is reduced;
a mesh plate, the mesh plate having a diameter larger than the inside diameter of the lower portion of the container and smaller than the diameter of the packing ring, the mesh plate configured to be placed on the annular surface of the stepped portion, and wherein the mesh plate has a mesh network configured to allow a liquid to pass through the mesh network; and
wherein when the container is sealed with the lid, a space configured to preserve the fragile object is formed between the mesh plate and the seal extending from the lid.

2. The device according to claim 1, wherein the packing ring includes a groove on a surface of the packing ring, the groove being perpendicular to the packing ring in a circumferential direction.

3. The device according to claim 1, wherein the seal is pressed by the lid and the packing ring on the stepped portion when the lid is screwed onto the container.

4. The device according to claim 1, wherein the opening of the upper portion is sealed with the lid simultaneously with or after sealing of the opening of the lower portion by the seal.

5. The device according to claim 1, wherein the fragile object is a sheet cell culture.

6. The device according to claim 5, wherein the sheet cell culture is a laminated body.

7. The device according to claim 1, wherein the packing ring is configured to keep the seal extending from the lid from contacting the mesh plate when the lid is screwed onto the container.

8. The device according to claim 1, wherein the mesh plate is configured to be removed from the container.

9. A device, the device comprising:
a container, the container having a cylindrical shape including a bottom, a lower portion, an upper portion having an opening, and an annular stepped portion extending from the lower portion of the container to the upper portion of the container, the annular stepped portion including an annular surface having a width obtained by a difference between an inside diameter of the upper portion of the container and an inside diameter of the lower portion of the container;
a packing ring configured to be received on the annular surface of the stepped portion of the container, the packing ring having a diameter smaller than the inside diameter of the upper portion of the container and larger than the inside diameter of the lower portion of the container;
a lid configured to seal the opening of the upper portion of the container;
a seal, the seal representing a portion being interposed between the lid and the stepped portion, the seal extending from the lid and having an outside diameter larger than an inside diameter of the lower portion of the container, and wherein the outside diameter of the seal is smaller than the inside diameter of the upper portion of the container, such that, upon inserting the seal into the container, a space is created between an outer periphery of the seal, an outer periphery of the packing ring, and an inner periphery of the upper portion of the container, and wherein the seal is configured to seal an opening of the lower portion of the container by a bottom surface of the seal coming into contact with the packing ring on the annular surface of the stepped portion;

wherein the inside diameter of the upper portion of the container is larger than the inside diameter of the lower portion of the container;

a space in the lower portion represents a housing space surrounded by the lower portion of the container, a space in the upper portion represents a space surrounded by the upper portion of the container, an opening of the space in the lower portion represents a boundary edge between the space in the lower portion and the stepped portion, and an opening of the space in the upper portion represents an end of the space in the upper portion;

a mesh plate, the mesh plate having a diameter larger than the inside diameter of the lower portion of the container and smaller than the diameter of the packing ring, the mesh plate configured to be placed on the annular surface of the stepped portion, and wherein the mesh plate has a mesh network configured to allow a liquid to pass through the mesh network; and wherein when the container is sealed with the lid, a space configured to preserve a fragile object is formed between the mesh plate and the seal extending from the lid.

10. The device according to claim 9, wherein the packing ring includes a groove on a surface of the packing ring, the groove being perpendicular to the packing ring in a circumferential direction.

11. The device according to claim 10, wherein the seal is pressed by the lid and the packing ring on the stepped portion when the lid is screwed onto the container.

12. The device according to claim 9, wherein the annular stepped portion is parallel to the bottom surface of the container.

13. The device according to claim 9, wherein the seal has a columnar shape and extends from a top board of the lid; and the lid includes a cylindrical sidewall extending downward from a peripheral edge of the top board, and an engagement portion protruding and disposed on an inner surface of the cylindrical sidewall.

14. The device according to claim 9, further comprising:
a liquid, the liquid being poured into the container until the liquid rises above the stepped portion; and
the fragile object.

15. The device according to claim 9, wherein the lid includes an internal thread disposed on an inner periphery of a cylindrical sidewall, the internal thread configured to be screwed into an external thread disposed on an outer periphery of the upper portion of the container; and
wherein a height of a seal from a top board of the lid is smaller than a height of the upper portion.

16. The device according to claim 9, further comprising:
an annular groove disposed on a lower surface of the seal, the annular groove configured to receive the packing ring.

17. The device according to claim 9, further comprising:
a recess disposed in the stepped portion of the container, the recess configured to hold a liquid pushed out from the container.

18. The device according to claim 9, wherein the lid includes a protrusion that protrudes downward from a bottom surface of the seal when the lid is attached to the container, the protrusion having a dome shape, including a vertex that has a horizontal sectional area tapering perpendicularly downward.

19. The device according to claim 9, wherein the packing ring is configured to keep the seal extending from the lid from contacting the mesh plate when the lid is screwed onto the container.

20. A method for preserving a fragile object, the method comprising:
pouring a liquid in a lower portion of a container until the liquid rises above an elastic packing ring on an annular surface of a stepped portion of the container, the stepped portion being between a lower portion of the container and an upper portion of the container, the stepped portion including the annular surface having a width obtained by a difference between an inside diameter of the upper portion of the container and an inside diameter of the lower portion of the container, the inside diameter of the upper portion of the container being larger than the inside diameter of the lower portion of the container, and the packing ring having a diameter smaller than the inside diameter of the upper portion of the container and larger than the inside diameter of the lower portion of the container;

arranging a mesh plate on the annular surface of the stepped portion of the container and inside of the packing ring, the mesh plate having a diameter larger than the inside diameter of the lower portion of the container and smaller than the diameter of the packing ring;

placing the fragile object into the liquid in the container;

interposing a seal between a lid configured to seal an opening of the upper portion of the container and the packing ring on the stepped portion, the seal representing a portion being interposed between the lid and the stepped portion, the seal extending from the lid and having an outside diameter larger than the inside diameter of the lower portion of the container, the outside diameter of the seal being smaller than the inside diameter of the upper portion of the container;

covering the container with the lid and the seal to raise a level of the liquid in the lower portion of the container and pushing the liquid from the container into a space between an outer periphery of the seal, an outer periphery of the packing ring, and an inner periphery of the container until a bottom surface of the seal and the packing ring on the annular surface of the stepped portion come into contact with each other at a same time the lid is attached to the container; and preserving the fragile object between the mesh plate and the seal extending from the lid.

* * * * *